US00PP31034P2

(12) United States Plant Patent
Carruth

(10) Patent No.: US PP31,034 P2
(45) Date of Patent: Nov. 12, 2019

(54) GROUND COVER ROSE PLANT NAMED 'WEKHAPLAMELBA'

(50) Latin Name: *Rosa hybrida*
Varietal Denomination: WEKhaplamelba

(71) Applicant: Early Morning LLC, Lawrenceburg, IN (US)

(72) Inventor: Thomas F. Carruth, Altadena, CA (US)

(73) Assignee: Early Morning, LLC, Lawrenceburg, IN (US)

( * ) Notice: Subject to any disclaimer, the term of this patent is extended or adjusted under 35 U.S.C. 154(b) by 0 days.

(21) Appl. No.: 16/350,473

(22) Filed: Nov. 19, 2018

(51) Int. Cl.
*A01H 5/02* (2018.01)
*A01H 6/74* (2018.01)

(52) U.S. Cl.
USPC ..... Plt./106
CPC ..... *A01H 6/74* (2018.05)

(58) Field of Classification Search
USPC ..... Plt./106, 105
CPC ..... A01H 5/0222
See application file for complete search history.

(56) References Cited

U.S. PATENT DOCUMENTS

PP19,646 P2 1/2009 Ilsink

OTHER PUBLICATIONS

Weeks Roses, "All Dressed Up", Wholesale Rose Catalog, 86 pages, 2019.

*Primary Examiner* — Kent L Bell
(74) *Attorney, Agent, or Firm* — McKee, Voorhees & Sease, PLC

(57) ABSTRACT

A new variety of Ground Cover rose suitable for garden decoration, having flowers of salmon coloration.

1 Drawing Sheet

Classification: The present invention relates to a new *Rosa hybrida* plant.

Variety denomination: The new plant has the varietal denomination 'WEKhaplamelba'.

BACKGROUND OF THE INVENTION

This invention relates to a new and distinct variety of Ground Cover Rose. It has as its seed parent the variety known as 'INTERhappy' (U.S. Plant Pat. No. 19,646) and a non-disseminated seedling of my creation as its pollen parent with the following genetic origin 'Playboy' x ('Mellow Yellow' x 'Baby Love').

SUMMARY OF THE INVENTION

Among the features which distinguish the new variety from other presently available and commercial rose cultivars known to the inventor are the following combinations of characteristics: its low spreading growing habit, its abundant blooms and its large clusters with multiple flowers. The plant has a low spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKhaplamelba' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'INTERhappy' by the following combination of characteristics: whereas 'WEKhaplamelba' bears semi-double flowers (about 6 to 9 petals) of salmon coloration, 'INTERhappy' bears single flowers of yellow-orange coloration with lesser petalage (about 6 petals). The new variety has a spreading low growing habit (about 23 to about 42 cm. in height), whereas the seed parent has a sprawling significantly taller growing habit (about 60 cm. in height).

The new variety may be distinguished from its pollen parent, a non-disseminated seedling of my creation by the following combination of characteristics: whereas 'WEKhaplamelba' bears semi-double flowers (about 6 to 9 petals) of salmon coloration, the non-disseminated seedling bears double flowers of bright yellow coloration with significantly heavier petalage (about 14 to 18 petals). The new variety has a spreading low growing habit (about 23 to about 42 cm. in height), whereas the pollen parent has a rounded bushy significantly taller growing habit (about 45 to about 60 cm. in height).

COMPARISON WITH THE CLOSEST COMMERCIALLY AVAILABLE CULTIVAR

The closest commercially available cultivar to the new variety is the seed parent 'INTERhappy' (U.S. Plant Pat. No. 19,646).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of October. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety sometimes bears its flowers singly, usually in clusters of four to eight or more per stem. Flowers may be borne in regular rounded clusters on strong somewhat short to medium length stems (about 13 to about 34 cm.). The cluster ranges from about 6.9 to about 10.6 cm. in diameter. Outdoors, the plant blooms abundantly and nearly continuously during the growing season. The flowers have a slight tea with hints of spices fragrance.

BUD

The peduncle is about 0.8 to about 2.2 cm. in length, of slender to average caliper (about 0.1 to about 0.2 cm. in diameter), and usually erect. It is moderately rough, with some stipitate glands, and few hairs. Peduncle color is between 146C and 146B often moderately suffused, especially on the side exposed to the sun, with between 187B and 187A.

Before the calyx breaks, the bud is about 0.5 to about 0.9 cm. in diameter at the widest point, about 0.8 to about 1.4 cm. in length, and pointed to somewhat ovoid in shape. The surface of the bud bears between 1 to 4 foliaceous appendages, few stipitate glands and many hairs, usually with slender entire foliaceous parts extending beyond the tip of the bud about ½ or more of its length. Bud color is between 137C and 146B often moderately suffused, especially on the side exposed to the sun, with between 187A and 187B.

The sepals are 5 per flower, about 1.1 to about 1.9 cm. in length and about 0.4 to about 0.5 cm. in width at the widest point. The outer surface color of the sepal is between 137C and 146B often moderately suffused, especially on the side exposed to the sun, with between 187A and 187B. The outer surface of the sepal is moderately smooth and bears between 0 to 2 foliaceous appendages with few stipitate glands and some hairs. The inner surface color of the sepal is near 146C broadly bordered by near 137A. After the sepals open, the inner surface color is sometimes lightly suffused, especially on the area exposed to the sun, with between 187A and 187B. The inner surface of the sepal is covered with fine wooly tomentum; sepal margins are entire and lined with few stipitate glands and hairs. The sepals are moderately fugacious, and usually straight in shape with acute apices.

The receptacle of the flower is of medium to somewhat long length (about 0.4 to about 0.6 cm.) and average in caliper (about 0.4 to about 0.6 cm. in diameter). The receptacle is urn-shaped in form. Its surface is smooth with few hairs and stipitate glands and with thick fleshy walls. The receptacle color is between 144A and 146B sometimes lightly suffused, especially on the side exposed to the sun, with between 187A and 187B.

As the petals open (after the calyx breaks), the bud is about 0.8 to about 1.4 cm. in diameter at the widest point, about 1.2 to about 1.7 cm. in length, and pointed to moderately ovoid in form. The color of the under surfaces of the newly opened petals is between 47B and 41D often moderately suffused with between 53C and 53B. At the point where the petal attaches, there is a moderately small zone of between 154C and 1C. The color of the upper surfaces of the newly opened petals is between 33A and 40B often lightly suffused with between 53C and 53B. At the point where the petal attaches, there is a moderately small zone of near 4B.

BLOOM

When fully open, the bloom ranges from about 2.9 to about 4.6 cm. in diameter. Petalage is semi-double with about 6 to 9 petals and about 0 to 2 petaloids irregularly arranged. When partially open, the bloom form is moderately ovoid to cupped, and the petals are loosely cupped with petal edges somewhat reflexed outward. When fully open, the bloom form is moderately cupped to somewhat flat, and the petals are loosely cupped with petal edges moderately reflexed outward.

PETALS

The substance of the petals is moderately heavy and of somewhat thin to medium thickness, with upper surfaces slightly satiny and under surfaces slightly shiny. The petals are about 1.1 to about 2.4 cm. in length and about 1.0 to about 2.0 cm. in width at the widest point. Petal margins are entire.

The outer petals are broadly obovate in shape with rounded apices.

The inner petals are broadly oblanceolate in shape with rounded apices.

Petaloids are about 0.8 to about 1.9 cm. in length and about 0.5 to about 1.2 cm. in width at the widest point. Petaloids are shaped obovate with rounded apices.

NEWLY OPENED FLOWER

The under surface color of the outer, intermediate and inner petals is between 48B and 48C often moderately suffused with between 53C and 53B. At the point where the petal attaches, there is a moderately large zone of between 2C and 3D. The upper surface color of the outer, intermediate and inner petals is between 39B and 41D often lightly suffused with between 53D and 53C. At the point where the petal attaches, there is a somewhat large zone of between 4A and 3A.

The under and upper surface colors of the petaloids are similar in coloration to the upper and under surfaces of the intermediate and inner petals.

The general tonality of the newly opened flower is between 39B and 41D often lightly suffused with between 53D and 53C.

THREE-DAY-OLD FLOWER

The under surface color of the outer, intermediate and inner petals is between 61D and 48D often moderately suffused with near 61C. At the point where the petal attaches, there is a moderately large zone of near 4D. The upper surface color of the outer, intermediate and inner petals is between 55B and 50C sometimes lightly suffused with between 61C and 53C. At the point where the petal attaches, there is a moderately large zone of near 4D.

The under and upper surface colors of the petaloids are similar in coloration to the upper and under surfaces of the intermediate and inner petals.

The general tonality of the three-day-old flower is between 55B and 50C sometimes lightly suffused with between 61C and 53C.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 110) and are arranged regularly about the pistils; a few are mixed with petaloids. The filaments are of moderately short length (about 0.3 to about 0.7 cm.) most with anthers. Filaments are between 150B and 153C in color. The anthers are somewhat small to medium size for the class and all open approximately at the same time. Anther color when immature is near 22A on the external part and near 11D on the internal part. Anther color at maturity is near 163A on the external part and near 200A on the internal part. Pollen is moderate and between 18B and 16D in color.

FEMALE REPRODUCTIVE ORGANS

Pistils vary in number (average about 25). The styles are moderately even, somewhat short to average in length (about 0.3 to about 0.5 cm.), thin in caliper, and loosely bunched. Stigma color is between 10C and 11B. Style color is between 149D and 150D often heavily suffused with between 53A and 53B. Ovaries are usually all enclosed in the calyx. The ovaries are of small size and between 158A and 158B in color.

Hips have not been observed on this variety when grown in Pomona, Calif.

FOLIAGE

The compound leaves are usually comprised of three to seven leaflets and are borne abundantly. The five-leaflet leaves are about 3.8 to about 8.0 cm. in length and about 2.6 to about 5.2 cm. in width at the widest point, moderately leathery to somewhat crisp in texture on both sides, and glossy in finish on the upper side and semi-glossy in finish on the under side. The leaves have a pinnate venation pattern. The terminal leaflets are about 1.6 to about 2.8 cm. in length and about 0.9 to about 1.8 cm. in width at the widest point, shaped moderately oval with acuminate apices and rounded bases. Their margins are usually simply serrate.

The upper surface color of the mature leaf is between 139A and 147A. The under surface color of the mature leaf is between 147B and 146B. The under and upper colors of the leaf veins on the mature leaf are similar in coloration to the upper and under surfaces colors of the mature leaf. The upper surface color of the young leaf is between 137B and 137A, often heavily suffused with between 187A and 187B. The under surface color of the young leaf is between 146A and 137C, often heavily suffused with between 187A and 187B. The under and upper colors of the leaf veins on the young leaf are similar in coloration to the upper and under surfaces colors of the young leaf.

The rachis is about 2.0 to about 4.9 cm. in length, about 0.1 cm in width at the widest point, and moderately rough. The upper side is shallowly grooved with few hairs and stipitate glands on the edges of the grooves. The under side of the rachis is moderately rough with few stipitate glands and small prickles. The rachis color is near 146B on the under side and near 137B on the upper side, often heavily suffused on the young leaves with between 187A and 187B.

The stipules are about 0.6 to about 1.1 cm. in length and of medium width (about 0.3 to about 0.4 cm.) with somewhat short to medium length straight points that usually turn out at an angle of more than 45 degrees and sometimes recurve toward the stem. The under and upper surface color of the stipule is between 137A and 137B sometimes lightly suffused on the young leaves with between 187A and 187B. The upper and under surfaces of the stipules are smooth in texture.

The petiole is light in caliper and moderately rough. The upper side is shallowly grooved with few hairs and stipitate glands on the edges of the grooves. The under side of the petiole is moderately rough with few stipitate glands and small prickles. The petiole is about 0.7 to about 1.1 cm. in length and about 0.1 cm in width at the widest point. The petiole color is near 146B on the under side and near 137B on the upper side, often heavily suffused on the young leaves with between 187A and 187B.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has a spreading low growing habit (about 23 to about 42 cm. in height and about 75 to about 120 cm. spread at the widest point), with full branching. It displays moderately vigorous growth and the canes are of somewhat light to medium caliper for the class (about 0.7 to about 1.1 cm. in diameter at the widest point).

The color of the major stems is between 146A and 137C. The major stems are rough in texture and they bear few large prickles that are about 0.4 to about 0.8 cm. in length. The large prickles are angled slightly downward with a moderately short broad oval base; prickle color is between 165A and 177B often moderately suffused with between 201B and 201C. The major stem bears few small prickles of similar shape and coloration.

The color of the branches is between 137C and 146A. The branches are rough in texture and they bear few large prickles which are of similar size and shape to the large prickles on the major stems; prickle color is between 177A and 165A. The branches bear few small prickles of similar shape and coloration.

The color of the new shoots is between 146C and 146B often moderately suffused with between 187B and 187A. The new shoots are rough in texture and they bear few large prickles which are of similar size and shape to the large prickles on the major stems; prickle color is between 187C and 187B. The shoots bear few small prickles of similar shape and coloration.

I claim:

1. A new and distinct Ground Cover rose plant of the variety substantially as described and illustrated herein.

* * * * *

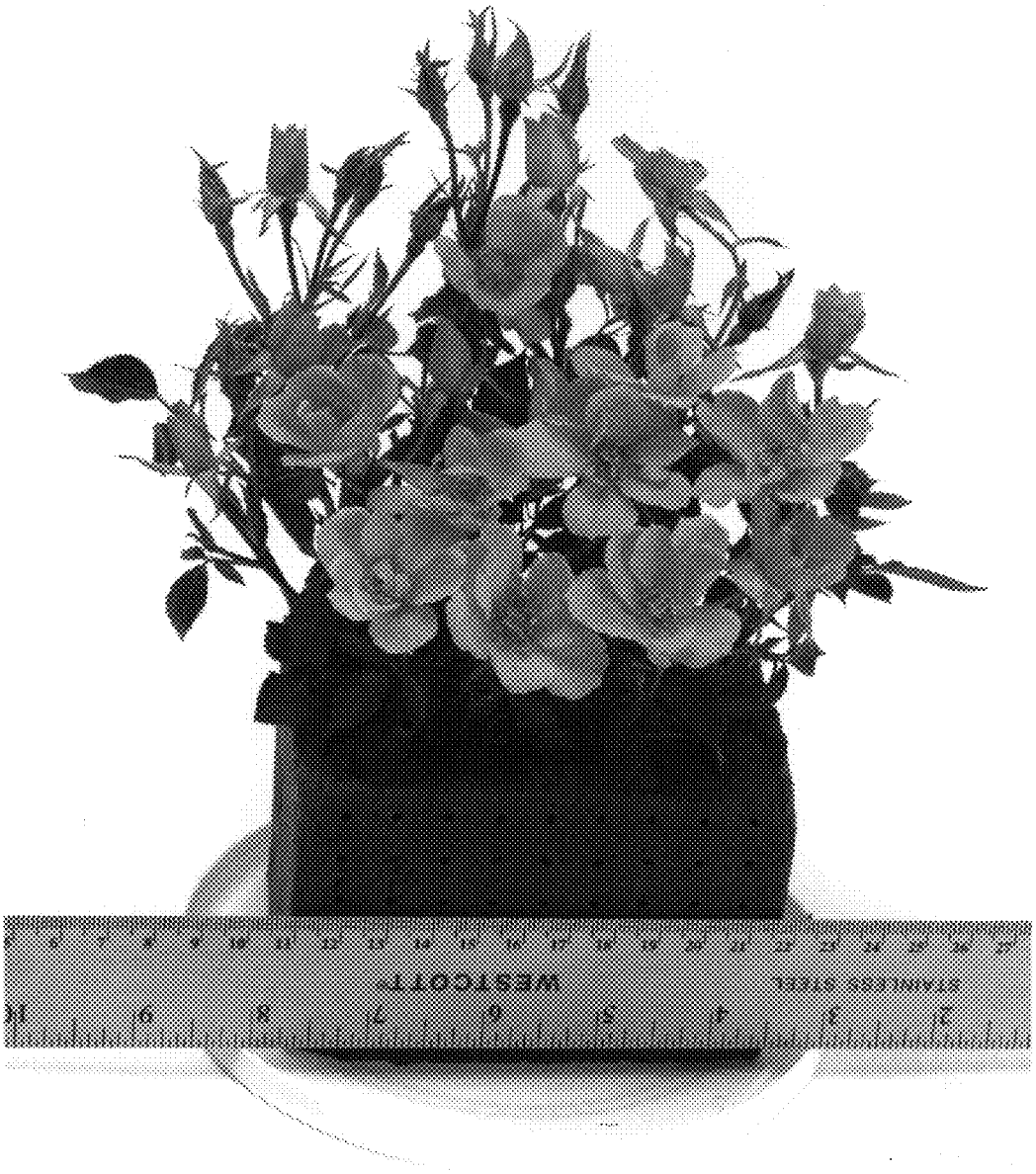
WESTCOTT
STAINLESS STEEL